United States Patent
Pesenti et al.

(10) Patent No.: US 10,518,017 B2
(45) Date of Patent: Dec. 31, 2019

(54) REGIONAL ANT-COAGULATION SYSTEM FOR AN EXTRACORPOREAL CIRCULATION CIRCUIT

(71) Applicant: Xenios AG, Heilbronn (DE)

(72) Inventors: Antonio Pesenti, Milan (IT); Alberto Zanella, Milan (IT); Domenico Salerno, Milan (IT); Francesco Mantegazza, Milan (IT); Vittorio Scaravilli, Milan (IT); Luigi Castagna, Lissone (IT)

(73) Assignee: Xenios AG, Heilbronn (DE)

( * ) Notice: Subject to any disclaimer, the term of this patent is extended or adjusted under 35 U.S.C. 154(b) by 236 days.

(21) Appl. No.: 15/538,492

(22) PCT Filed: Dec. 23, 2015

(86) PCT No.: PCT/IB2015/059947
§ 371 (c)(1),
(2) Date: Jun. 21, 2017

(87) PCT Pub. No.: WO2016/103216
PCT Pub. Date: Jun. 30, 2016

(65) Prior Publication Data
US 2017/0348472 A1    Dec. 7, 2017

(30) Foreign Application Priority Data

Dec. 23, 2014   (IT) .............................. TO2014A1096

(51) Int. Cl.
*A61M 1/34*   (2006.01)
*A61M 1/36*   (2006.01)
*B01D 15/36*  (2006.01)

(52) U.S. Cl.
CPC ........ *A61M 1/3479* (2014.02); *A61M 1/3413* (2013.01); *A61M 1/3672* (2013.01); *B01D 15/362* (2013.01)

(58) Field of Classification Search
CPC .............. A61M 1/3413; A61M 1/3472; A61M 1/3479; A61M 1/3486; A61M 1/3672; A61M 1/3675; B01D 15/362
See application file for complete search history.

(56) References Cited

U.S. PATENT DOCUMENTS 3,579,441 A * 5/1971 Brown ................ A61M 1/3472
                                                            128/898
2011/0168614 A1  7/2011 Pouchoulin
(Continued)

FOREIGN PATENT DOCUMENTS

DE   102012020497 A1   4/2014
FR       1312112 A    12/1962
(Continued)

OTHER PUBLICATIONS

International Search Report and Written Opinion issued in PCT/IB2015/059947, dated Mar. 29, 2016, 13 pages.
(Continued)

*Primary Examiner* — Kai H Weng
(74) *Attorney, Agent, or Firm* — Dinsmore & Shohl LLP

(57) ABSTRACT

The present invention concerns an extracorporeal circuit for regional scoagulation of blood comprising a line for taking the blood from the patient, a first filtering unit, and a line for returning the blood to the patient defining a main circuit, the extracorporeal circuit comprising a secondary circuit for recirculation of the plasma water comprising:
  a calcium removal assembly adapted to provide a solution with low calcium content in said main circuit;
the extracorporeal circuit further comprising:
(Continued)

first means for the infusion of said solution with low calcium content into said main circuit upstream of said first filtering unit and of said calcium removal assembly with respect to the blood flow direction in the main circuit and second means for the infusion of an electrolytic re-establishment solution located downstream of said first means with respect to the direction of the blood flow in said main circuit.

5 Claims, 3 Drawing Sheets

(56) References Cited

U.S. PATENT DOCUMENTS

| | | | |
|---|---|---|---|
| 2011/0237996 A1* | 9/2011 | Kotanko | A61M 1/16 604/6.07 |
| 2011/0264025 A1 | 10/2011 | Lannoy | |
| 2014/0158588 A1 | 6/2014 | Pudil et al. | |
| 2014/0217028 A1* | 8/2014 | Pudil | A61M 1/1696 210/646 |

FOREIGN PATENT DOCUMENTS

| | | |
|---|---|---|
| IT | BO20090437 A1 | 1/2011 |
| WO | 2008135282 A2 | 11/2008 |
| WO | 2011130528 A1 | 10/2011 |
| WO | 2016016870 A1 | 2/2016 |

OTHER PUBLICATIONS

Machine translation of Hemodec (IT BO20090437), using Google Translate (Year: 2019).

* cited by examiner

REGIONAL ANT-COAGULATION SYSTEM FOR AN EXTRACORPOREAL CIRCULATION CIRCUIT

TECHNICAL FIELD

The present invention concerns a system for regional scoagulation of blood in an extracorporeal circulation circuit during the application of extracorporeal support techniques.

BACKGROUND ART

The possibilities of use for clinical purposes of techniques for extracorporeal treatment of blood are extremely varied; they comprise a wide group of therapies which include intermittent or continuous renal support, apheresis and haemoperfusion treatment for removal of cytokines or toxins, the various techniques of extracorporeal support for the vital functions (known also as Extracorporeal Life Support or ECLS) including ExtraCorporeal Membrane Oxygenation or ECMO, veno-arterial for cardiac support or veno-venous for respiratory support, and the techniques for extracorporeal removal of carbon dioxide ($ECCO_2R$).

All types of therapy entailing extracorporeal treatment of the blood also require the administration of an anticoagulant treatment, since the artificial surfaces are not able to reproduce the biocompatibility existing between blood and blood vessels. In the absence of this treatment, also known as scoagulation, the contact of the blood with the surfaces of the circuits causes activation of the coagulation cascade and leads to progressive thrombosis of the circuit with consequent loss of the extracorporeal support function and possible embolism of the thrombi.

The known strategies for scoagulating the blood in extracorporeal treatments are divided into systemic and regional: the former are aimed at scoagulating all the patient's blood; the latter are aimed at performing a scoagulation targeted only at the level of the extracorporeal circuit; each of the two strategies has advantages and disadvantages.

Systemic scoagulation is the strategy that has been used longest and is the most widespread; its main advantage is applicability to all the extracorporeal blood flow regimes, but it exposes the patient to an increased risk of bleeding. It is normally obtained by means of continuous parenteral infusion of unfractionated heparin, which guarantees a rapid on-set, a brief half-life, reversibility of the effect and low costs. The disadvantage of this drug is the poor predictability of the clinical effect and consequently the need for strict monitoring with laboratory tests; furthermore, it is not free from side effects such as heparin-induced thrombocytopenia.

To obtain systemic scoagulation, low molecular weight heparin is also used, administered by subcutaneous injections. It has a more predictable dose-effect relation than unfractionated heparin, but it does not allow monitoring of the anticoagulant effect.

Other systemic anticoagulants, such as the direct thrombin or X factor inhibitors, are used only rarely in the case of contraindications to heparin; they do not significantly reduce the risk of bleeding with respect to the heparin and they are more costly.

In recent years, to avoid the complications of systemic anticoagulant treatments, regional scoagulation techniques have been developed which limit the anticoagulant effect to the blood present only in the extracorporeal circuit.

One of these techniques entails the infusion of citrate immediately after the blood taken from the patient enters the extracorporeal circuit, which is then antagonised by the infusion of calcium chloride before returning the blood to the patient.

An alternative technique is to provide infusion of unfractionated heparin into the circuit, antagonised by the infusion of protamine before returning the blood to the patient.

The infusion of heparin-protamine is not widely used since, in addition to the known problems with the systemic administration of heparin, there are also problems due to the infusion of a drug, protamine, with a low therapeutic index, which has cardiovascular complications and can cause anaphylactic reactions.

Regional scoagulation obtained by infusion of citrate, on the other hand, is a technique which has become widespread in recent years. This technique is based on the capacity of the citrate anion to chelate the blood calcium, which represents an essential factor for functionality of the coagulation cascade. The citrate is infused at the beginning of the circuit mainly in the form of sodium citrate, while the calcium is re-infused at the end of the circuit in the form of calcium chloride, so that the blood returns to the patient with a normal coagulation functionality.

Examples of circuits in which citrate is used as an anticoagulant system are described in US2011168614 and US2011264025.

The main drawback of the use of citrate is the fact that the majority of the citrate infused reaches the systemic circulation of the patient and consequently must be eliminated by the patient by means of metabolisation (mainly hepatic).

Even when the patient has normal citrate clearance, and often this is not the case in critical patients, it is not possible to scoagulate extracorporeal blood flows higher than 200 ml/min since it would require doses of citrate higher than the patient's clearance capacity and consequently the citrate would accumulate in the patient, leading to severe side effects.

In addition to this problem, it is also difficult to control the concentration of the sodium administered as counter ion of the citrate, which is infused in the form of trisodium citrate.

Other systems for scoagulation of the extracorporeal blood are illustrated in DE102012020497 and WO2011130528. These systems provide a calcium removal unit positioned directly along the main line of the blood. One of the drawbacks associated with this configuration is the fact that to scoagulate a clinically significant entire blood flow, the device must have large dimensions, thus increasing the priming volume of the circuit. Furthermore, since the calcium removal system is positioned on the blood line, it has to be extremely biocompatible and in any case the blood upstream of the calcium removal unit is not coagulated. Lastly, when the calcium removal unit is an ionic resin, it is not possible to filter any fragments released by it into the blood since the latter cannot be filtered by appropriate fine mesh filters.

The need was therefore felt in the art to find an alternative strategy to obtain regional scoagulation of the blood which is free from the drawbacks of the known techniques.

DISCLOSURE OF INVENTION

The object of the present invention is therefore to provide an alternative strategy to obtain effective and safe regional scoagulation of the blood. The terms scoagulate, scoagulation, scoagulating and scoagulated as used in this disclosure are herein defined respectively as anti-coagulate, anti-coagulation, anti-coagulating and anti-coagulated.

Said object is achieved by the present invention which concerns an extracorporeal circulation system according to claim 1 and the preferred and/or auxiliary characteristics of which are described in claims 2 to 5.

Specifically an extracorporeal circuit is provided for regional scoagulation of the blood comprising a line for taking the blood from the patient, a filtering unit and a line for returning the blood to the patient defining a main circuit.

The extracorporeal circuit of the invention further comprises a secondary circuit for recirculating the plasma water comprising:
- a calcium removal assembly adapted to provide a solution with a low calcium content in the main circuit.

The extracorporeal circuit of the invention further comprises:
- first means for infusion of the solution with low calcium content into the main circuit upstream of the first filtering unit and the calcium removal assembly with respect to the blood flow direction in the main circuit and
- second means for infusion of a solution with high calcium content located downstream of the first means with respect to the blood flow direction in said main circuit.

Advantageously said embodiment allows the entire extracorporeal circuit to be scoagulated in a simple safe manner.

In one embodiment, the calcium removal assembly can comprise ionic exchange resins or, alternatively, an electrodialyser to remove the calcium from the blood.

The reduction of the calcium from the extracorporeal blood therefore allows an anticoagulant effect to be obtained, which is then antagonised by the infusion of calcium immediately before returning the blood to the patient.

The first filtering unit can be selected from the group consisting of a haemodiafilter, a haemofilter, a dialyser and a plasma filter.

The calcium removal assembly can include a cartridge comprising an ionic exchange cationic resin loaded with sodium, potassium, chlorine and bicarbonate or alternatively a precipitate removal unit and an electrodialyser arranged in series.

BRIEF DESCRIPTION OF THE DRAWINGS

The present invention will now be described in detail with reference to the figures of the accompanying drawings, in which.

BEST MODE FOR CARRYING OUT THE INVENTION

Figure 1:
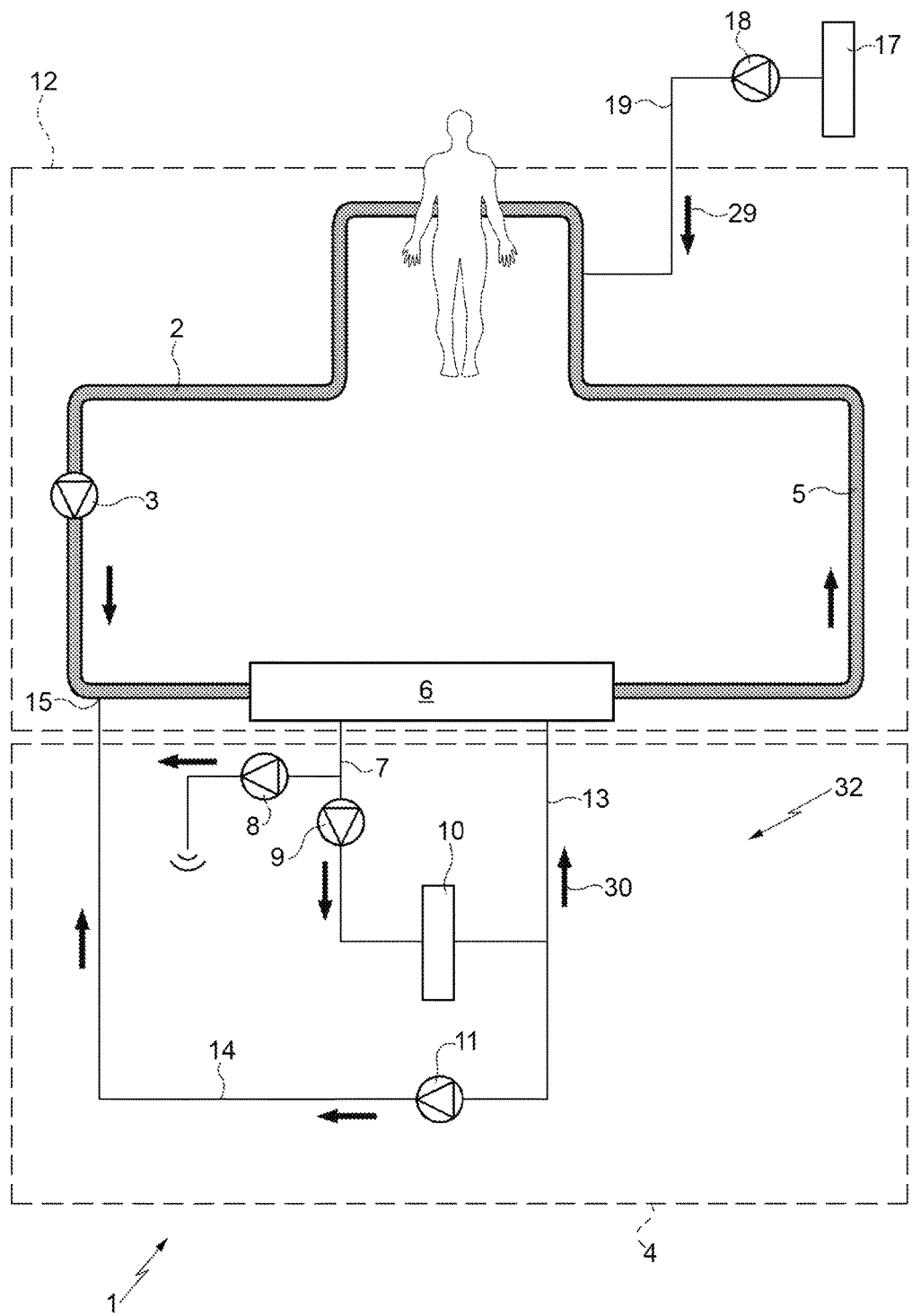
FIG. 1 illustrates a first embodiment of the invention.

In FIG. 1 the number 1 indicates as a whole an extracorporeal circulation system according to a first embodiment of the present invention.

The circuit 1 comprises a line for taking the blood 2 from the patient, on which a peristaltic pump 3 acts, a first filtering unit 6 and a line for returning the blood 5 to the patient, which define a main circuit 12.

In the embodiment illustrated in FIG. 1, the first filtering unit 6 is a haemofilter.

The circuit 1 further includes a calcium removal assembly 4 which comprises a cartridge 10 including an ionic exchange cationic resin for the calcium previously loaded with a solution of sodium, potassium, chlorine and bicarbonate.

In use, the blood removed from the patient via the line 2 is sent, by the action of the pump 3, to the haemofilter 6. The haemofilter 6 separates the plasma water which is conveyed via the line 7, by means of the pump 9, to the ionic exchange cationic resin 10 in which the calcium ions are removed, generating a solution 30 with low calcium content. Said solution 30 is enriched with sodium ions exchanged by the resin 10 in return for the calcium ions removed by said resin 10.

A fraction of the solution 30 with low calcium content is sent back to the main circuit 12 at the haemofilter 6 via the line 13.

A fraction of the solution 30 with low calcium content can be recirculated at the re-joining point 15 arranged on the line 2 upstream of the haemofilter 6 with respect to the blood flow direction in the main circuit 12 via the line 14 by the action of the pump 11. Said line 14 can be connected to the line 2 both before and after the pump 3.

In this embodiment, the solution with low calcium content 30, by diluting the blood flow in the line 2 and circulating in the haemofilter 6, allows dilution and reduction of the calcium concentration in the blood until obtaining scoagulation thereof.

To maintain the sodium balance, since the resin 10 retains the calcium but releases sodium into the plasma water, it is further possible to remove part of the plasma water, for example along line 7 or alternatively along line 13, by the action of the pump 8. In this case, the quantity of plasma water removed by the pump 8 must be such as to contain a quantity of sodium corresponding to the quantity released by the resin 10 in the same unit of time, in order not to increase the concentration of sodium returned to the patient. Alternatively, it is possible to fit along the line 13 a fine mesh filter able to retain any fragments released by the cartridge 10.

To restore the hydro-electrolytic balance of the remaining ions involved in the process, before the blood is returned to the patient, along the line 5, and the normal haematic concentration of calcium, in addition to magnesium, potassium and chlorine, an electrolytic re-establishment solution 29, contained in the bag 17, is infused via the line 19 by means of a pump 18. Alternatively said solution 29 contained in the bag 17 can be infused to a central or peripheral venous access in order to restore the systemic hydro-electrolytic balance.

For example, said solution 29 can contain cations at a concentration ranging from approximately 125 to 175 mEq/L, in particular in the form of calcium (110 to 140 mEq/L), magnesium (10 to 40 mEq/L) and a small quantity of potassium, corresponding to the plasma concentration range (2 to 5 mEq/L). The solution 29 can further contain anions in a concentration ranging from 125 to 175 mEq/L in particular in the form of chlorides (90 to 120 mEq/L) and organic ions (for example bicarbonates, lactates, acetates, gluconates) in order to achieve electroneutrality of said solution (60 to 30 mEq/L).

The quantity of the solution 29 infused in the unit of time corresponds to the volume removed through line 7 by means of the pump 8, thus maintaining the hydro-electrolytic balance.

The extracorporeal circuit 1 described above can therefore be easily integrated with the most appropriate devices for carrying out the extracorporeal therapy necessary to support the patient.

Said therapy can be, for example, a renal function replacement therapy, an extracorporeal removal of $CO_2$ or a removal of excess substances present in the blood, for example cytokines, toxins, myoglobin, lactate, electrolytes or drugs.

Said extracorporeal therapy can be performed by positioning the appropriate device along the line 5 downstream of the filtering unit 6 but upstream, in the direction of the blood flow in the main circuit 12, of the point where line 19 re-joins line 5. Alternatively, in the embodiment that entails recirculation of part of the solution 30 upstream of the filtering unit 6, the device for the extracorporeal therapy can be arranged on the line 2 between the re-joining point 15 and the filtering unit 6.

For example, if the device for the extracorporeal therapy is an artificial lung or a bubble oxygenator for the removal of carbon dioxide which require treatment of the plasma water, the device can be inserted along the line 7, 14 or 13.

If on the other hand the patient requires renal replacement therapy, it can be operated directly by selecting a haemofilter as filtering unit 6. This therapy can be performed in post-dilution infusing the renal replacement therapy solution directly into the blood line 5.

Alternatively, the renal replacement therapy can be performed in pre-dilution, infusing the renal replacement therapy solution into the line 2 upstream of the filtering unit 6 or into the line 14.

Where the renal replacement therapy is performed using a dialyser as the filtering unit 6, the renal replacement therapy solution can be infused into the line 13.

In the embodiment for renal replacement therapy, in order to maintain the scoagulation effect of the reduced calcium content, the renal replacement therapy solution shall preferably have an almost nil calcium content and a reduced sodium content to balance the release of sodium by the resin 10.

As regards the loss of plasma water necessary for performing the renal replacement therapy, this can be done through the line 7 by the pump 8, or alternatively the plasma water can be removed along the line 13.

The system of FIG. 1, in which the filtering unit 6 is a haemofilter, was tested in a pig model. The blood flow was set in a range from 150 to 400 ml/min, the flow into the pump 9 in a range from 600 to 2400 ml/min and the flow of the pump 11 in a range from 300 to 800 ml/min. Removal of the calcium by the calcium removal assembly 4 allowed the calcium concentrations to be reduced along the haematic circuit to values comparable with those obtained via the use of an administration of sodium citrate, obtaining a regional scoagulation, measured with an elongation of the activated clotting time—ACT.

Figure 2:
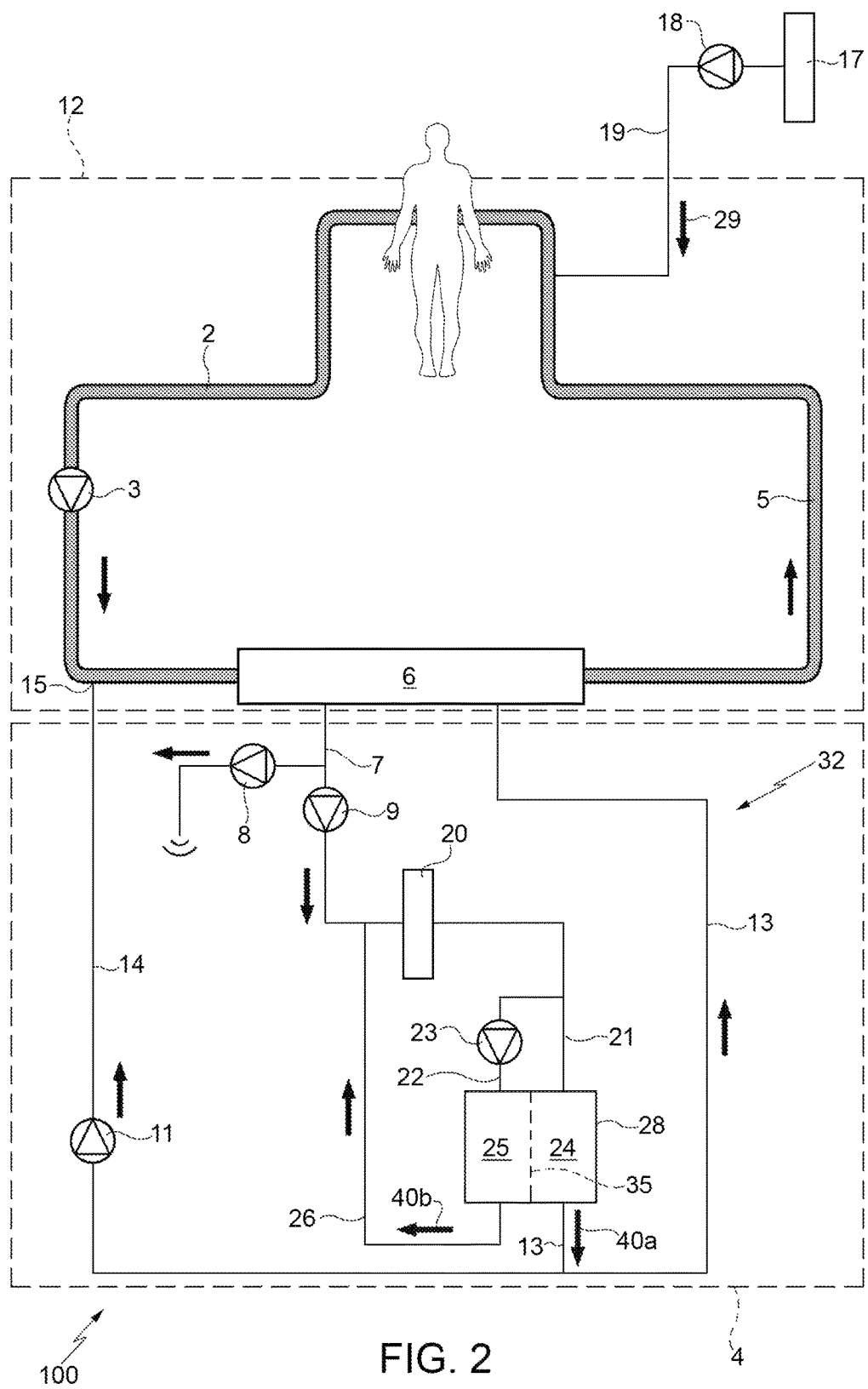
FIG. 2 illustrates a second embodiment of the invention.

FIG. 2 illustrates a second embodiment of the extracorporeal circuit 100 according to the present invention. The details similar or identical to those already described are indicated for the sake of simplicity by the same reference numbers.

In this embodiment, the circuit 100 comprises a calcium removal assembly 4 which in turn comprises an electrodialyser 28. In particular, the blood removed from the patient via the line 2 is sent, by the action of the pump 3, to the first filtering unit 6, in this case, for example, a haemodiafilter. The haemodiafilter 6 separates the plasma water which is conveyed via the line 7, by means of the pump 9, to the electrodialyser 28.

Figure 3:
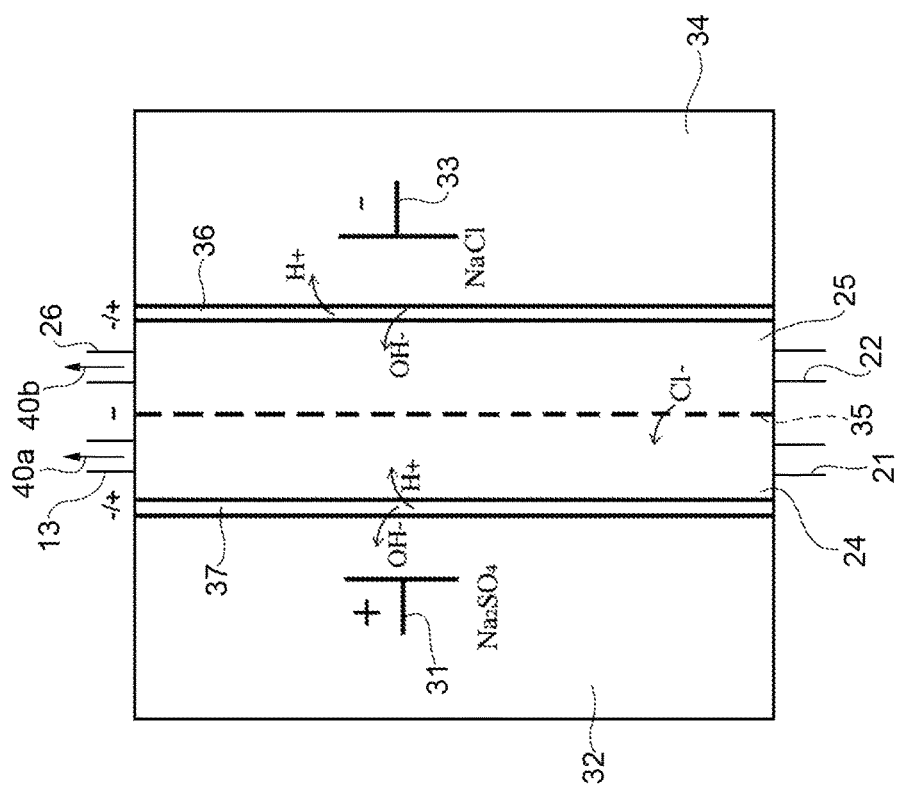
FIG. 3 illustrates a detail of the electrodialyser of the extracorporeal circulation system of FIG. 2. In said embodiment the electrodialyser is optimised with the application of a semipermeable membrane permeable to cations only.

As illustrated in FIG. 3, the electrodialyser 28 is provided with a first electrodialysis chamber 24 and a second electrodialysis chamber 25 separated by an ionic membrane 35.

Each chamber is separated from the corresponding electrode 31,33 by means of a bipolar membrane 36,37. The positive electrode 31, or anode, is arranged in a first chamber 32 immersed in a solution of anolyte, for example sodium sulphate or sodium phosphate, and the negative electrode 33, or cathode, is arranged in a second chamber 34 immersed in a solution of catholyte, for example sodium chloride.

According to FIG. 3, the ionic membrane 35 is a cationic membrane, the electrodialysis chamber 24 associated with the anode 31 is adapted to generate an acid solution and the electrodialysis chamber 25 associated with the cathode 33 is adapted to generate a basic solution.

As illustrated in FIG. 2, part of the plasma water, pushed by the pump 9, reaches the first chamber 24 of the electrodialyser 28, via the line 21. The remaining part of the plasma water is introduced into the second chamber 25 by the action of the pump 23 via the line 22.

Inside the electrodialyser, proportionally to the electrical current applied, the plasma water that enters the second chamber 25, i.e. the "basic" chamber, receives cations from the plasma water present in the first chamber 24, i.e. the "acid" chamber. Since the main cation in the plasma water is $Na^+$, the plasma water that flows in the second chamber 25 is enriched in $Na^+$ ions while the $OH^-$ ions are provided through the bipolar membrane 36. In the first chamber 24 a flow of an acid solution, the acid plasma water 40a, therefore forms, while in the second chamber 25 a flow of basic plasma water 40b forms.

Figure 4:
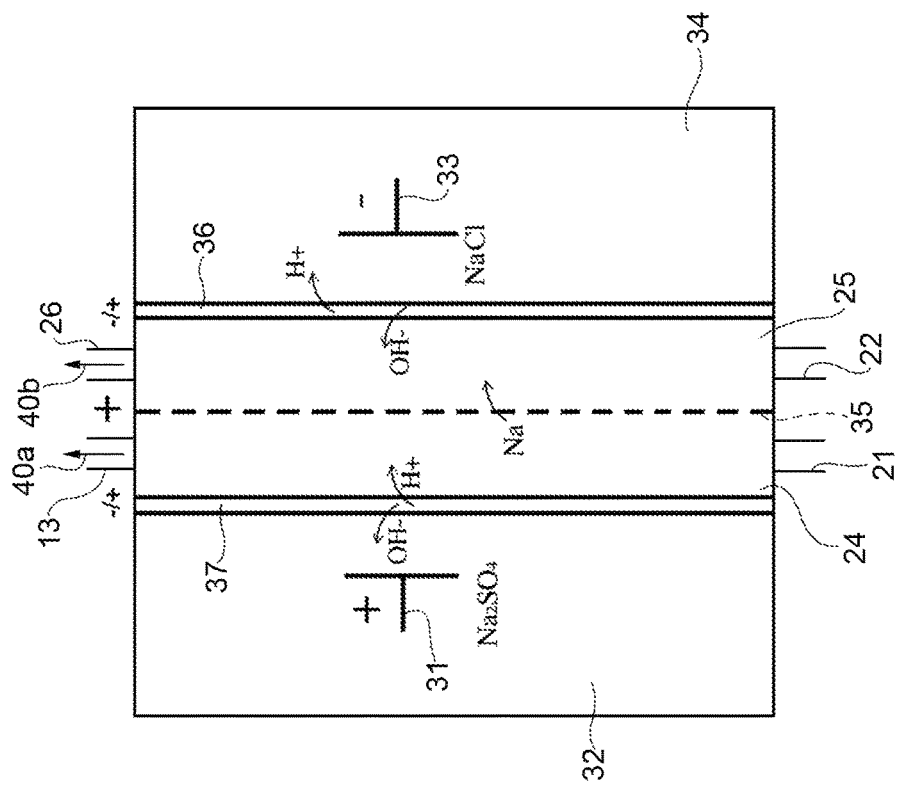
FIG. 4 illustrates a detail of the electrodialyser of the extracorporeal circulation system of FIG. 2. In said embodiment the electrodialyser is optimised with the application of a semipermeable membrane permeable to anions only.

Alternatively the ionic membrane 35 can be an anionic membrane, as illustrated in FIG. 4. In this case the flow of the ions into the electrodialyser 28 will be as shown.

In this case, the plasma water that enters the chamber 25, i.e. the basic chamber, releases anions to the solution present in the chamber 24, i.e. the acid chamber. Since the main anion in the plasma water is $Cl^-$, the solution that flows in the chamber 24 is enriched in $Cl^-$ ions, generating, proportionally to the electrical current applied, a solution rich in chlorine.

Other configurations of the electrodialyser 28 having, for example, a plurality of acid chambers and basic chambers are equally functional for the purpose of the present invention.

The application of an electrodialysis technique on the plasma water, whether a dialysate or an ultrafiltrate, allows the selective separation of anions and cations present in the solution.

The solution 40b generated by the chamber 25 is recirculated via the line 26 to the electrodialyser 28.

Upstream of the electrodialyser 28, on the recirculation circuit 7 of the plasma water, there is a calcium precipitate removal unit 20, for example a filter or a tangential filter or a centrifuge separator, to remove the precipitate. Said unit 20 is able to remove the calcium precipitates that form in the solution 40b, thus reducing the calcium content of the plasma water which is then returned to the filtering unit 6.

The solution 40a coming out of the chamber 24 is partly sent via the line 13 to the filtering unit 6 and partly via the line 2 by means of the pump 11 to the re-joining point 15 upstream of the filtering unit 6. The solution 40a therefore derives from the plasma water, the calcium concentration of which is reduced by the recirculation action of the solution 40b and the action of the unit 20. Therefore, the solution 40a which is returned to the main circuit at the re-joining point 15 and the solution provided inside the filtering unit 6 has a low calcium content and scoagulates the blood.

If necessary, by setting the appropriate process parameters, the calcium crystals can be subsequently re-dissolved by means of acidification and if necessary the calcium recovered can be re-infused into the patient.

Along the line 5, the normal blood concentration of calcium and magnesium will be obtained by infusion of a solution with high calcium content 29, contained in the bag 17, via the line 19 by means of a pump 18. The ion content of the bag 17 can be defined in the most appropriate way as required.

As for the circuit 1 previously described, the scoagulated blood can undergo the same extracorporeal treatment in the same positions along the line 2 or 5.

The invention claimed is:

1. An extracorporeal circuit for regional anti-coagulation of blood, comprising:
   a line for taking the blood from a patient, a first filtering unit, and a line for returning the blood to the patient defining a main circuit, the first filtering unit operable to separate plasma water from the blood;
   a secondary circuit for recirculation of the plasma water from the first filtering unit, the secondary circuit comprising:
      a calcium removal assembly configured to receive the plasma water from the first filtering unit and adapted to provide a solution with low calcium content with respect to the plasma water provided from the first filtering unit in the main circuit;
      a first line adapted to infuse the solution with low calcium content into the main circuit upstream of the first filtering unit and of the calcium removal assembly with respect to a blood flow direction in the main circuit; and
      a second line for infusion of an electrolytic re-establishment solution located downstream of the first line with respect to the direction of the blood flow in the main circuit.

2. The extracorporeal circuit for regional anti-coagulation of blood according to claim 1, wherein the first filtering unit is selected from the group consisting of a haemodiafilter, a haemofilter, a dialyser and a plasma filter.

3. The extracorporeal circuit for regional anti-coagulation of blood according to claim 1, wherein the calcium removal assembly comprises a cartridge comprising an ionic exchange cationic resin loaded with sodium, potassium, chlorine and bicarbonate.

4. The extracorporeal circuit for regional anti-coagulation of blood according to claim 1, wherein the calcium removal assembly comprises a precipitate removal unit and an electrodialyser arranged in series, the electrodialyser comprising a basic chamber adapted to generate a basic solution which is recirculated upstream of the precipitate removal unit to allow precipitation of the calcium, and an acid chamber adapted to generate a solution with low calcium content.

5. The extracorporeal circuit for regional anti-coagulation of blood according to claim 1, further comprising a line for returning a fraction of the solution with low calcium content provided by the calcium removal assembly to the main circuit at the first filtering unit.

* * * * *